(12) United States Patent
Liao

(10) Patent No.: US 10,906,819 B2
(45) Date of Patent: Feb. 2, 2021

(54) LIQUID SANITATION DEVICE AND METHOD

(71) Applicant: LARQ Inc., Foster City, CA (US)

(72) Inventor: Yitao Liao, Hayward, CA (US)

(73) Assignee: LARQ INC., Foster City, CA (US)

( * ) Notice: Subject to any disclaimer, the term of this patent is extended or adjusted under 35 U.S.C. 154(b) by 0 days.

(21) Appl. No.: 16/184,938

(22) Filed: Nov. 8, 2018

(65) Prior Publication Data

US 2019/0135660 A1     May 9, 2019

Related U.S. Application Data

(63) Continuation of application No. 29/626,652, filed on Nov. 17, 2017.

(Continued)

(51) Int. Cl.
*C02F 1/32*     (2006.01)
*A61L 2/10*     (2006.01)
(Continued)

(52) U.S. Cl.
CPC ............... *C02F 1/325* (2013.01); *A61L 2/10* (2013.01); *A61L 2/24* (2013.01); *C02F 1/003* (2013.01); *A61L 2202/11* (2013.01); *A61L 2202/121* (2013.01); *A61L 2202/122* (2013.01); *A61L 2202/14* (2013.01); *A61L 2202/16* (2013.01); *C02F 2201/006* (2013.01); *C02F 2201/326* (2013.01); *C02F 2201/3221* (2013.01); *C02F 2201/3222* (2013.01);
(Continued)

(58) Field of Classification Search
None
See application file for complete search history.

(56) References Cited

U.S. PATENT DOCUMENTS

| 4,694,179 A | 9/1987 | Lew et al. |
| D488,225 S | 4/2004 | Roberson |

(Continued)

FOREIGN PATENT DOCUMENTS

CN     104013306 B     1/2016

OTHER PUBLICATIONS

PCT Search Report Regarding Application No. PCT/US18/59875, dated Jan. 18, 2019.

(Continued)

*Primary Examiner* — Richard C Gurtowski
(74) *Attorney, Agent, or Firm* — Arc IP Law, PC; Joseph J. Mayo

(57) ABSTRACT

A method for a water bottle comprising, coupling a cap to bottle housing such that an interior of the water bottle and the cap form a water-tight region, receiving a button push on the cap, determining with a light sensor whether visible light is present in a vicinity of a UV LED light source disposed within the cap, in response to the push of the button, initiating providing with a UV LED light source UV light to the interior in response to the push of the button and in response to absence of the visible light within the vicinity of the UV LED light source, and inhibiting providing with the UV light to the interior after a period of time after the initiating providing UV light to the interior or in response to determining the visible light being present in the vicinity of the UV LED light source.

20 Claims, 3 Drawing Sheets

SECTION AA
110

Related U.S. Application Data

(60) Provisional application No. 62/583,447, filed on Nov. 8, 2017.

(51) Int. Cl.
*A61L 2/24* (2006.01)
*C02F 1/00* (2006.01)

(52) U.S. Cl.
CPC .............. *C02F 2201/3228* (2013.01); *C02F 2209/008* (2013.01); *C02F 2209/02* (2013.01); *C02F 2209/44* (2013.01); *C02F 2303/04* (2013.01); *C02F 2307/02* (2013.01); *C02F 2307/04* (2013.01)

(56) References Cited

U.S. PATENT DOCUMENTS

| | | | |
|---|---|---|---|
| 6,715,681 B2 | 4/2004 | Dvorkis et al. | |
| 6,857,304 B2 | 2/2005 | Enoki | |
| D651,086 S | 12/2011 | Gullickson et al. | |
| D658,998 S | 5/2012 | Simmons et al. | |
| D660,704 S | 5/2012 | Simmons et al. | |
| D660,705 S | 5/2012 | Simmons et al. | |
| D669,497 S | 10/2012 | Lee et al. | |
| D696,945 S | 1/2014 | Newman | |
| D705,063 S | 5/2014 | Weiss | |
| 8,816,300 B1 | 8/2014 | Walker et al. | |
| 8,872,130 B1 | 10/2014 | Matthews et al. | |
| D723,333 S | 3/2015 | Lin | |
| D724,621 S | 3/2015 | Rydenhag et al. | |
| D744,535 S | 12/2015 | Shin et al. | |
| D753,442 S | 4/2016 | Weernink | |
| D763,910 S | 8/2016 | Drozd et al. | |
| D772,014 S | 11/2016 | Ayres | |
| D790,279 S | 6/2017 | Izen et al. | |
| D796,956 S | 9/2017 | Clark et al. | |
| D798,315 S | 9/2017 | Prophete et al. | |
| D807,376 S | 1/2018 | Mizono | |
| D808,983 S | 1/2018 | Narinedhat et al. | |
| D813,245 S | 3/2018 | Mariet et al. | |
| D814,241 S | 4/2018 | Nickley et al. | |
| D821,410 S | 6/2018 | Vinna et al. | |
| D826,052 S | 8/2018 | Harris et al. | |
| D826,952 S | 8/2018 | Duriseti et al. | |
| 10,063,908 B2 | 8/2018 | Jain | |
| D830,784 S | 10/2018 | Moore et al. | |
| D837,807 S | 1/2019 | Baber et al. | |
| 2004/0068900 A1 | 4/2004 | Moran | |
| 2006/0151369 A1* | 7/2006 | Hegmegi | C02F 1/325 210/149 |
| 2006/0163169 A1 | 7/2006 | Eckhardt et al. | |
| 2013/0309131 A1* | 11/2013 | Engelhard | H05B 41/36 422/24 |
| 2016/0089457 A1* | 3/2016 | Liao | A61L 2/10 250/504 R |
| 2016/0270602 A1 | 9/2016 | Casey | |
| 2017/0224140 A1 | 8/2017 | Vertegaal et al. | |
| 2017/0280737 A1 | 10/2017 | Liao et al. | |

OTHER PUBLICATIONS

USPTO; Restriction Requirement dated Nov. 14, 2018 in U.S. Appl. No. 29/626,652.

USPTO; Non-Final Office Action dated Feb. 13, 2019 in U.S. Appl. No. 29/626,652.

USPTO; Notice of Allowance dated Apr. 6, 2020 in U.S. Appl. No. 29/626,652.

* cited by examiner

LIQUID SANITATION DEVICE AND METHOD

CROSS-REFERENCE TO RELATED APPLICATIONS

The present application claims priority to and is a non-provisional of U.S. Pat. App. No. 62/583,447, filed Nov. 8, 2017 and claims priority to U.S. patent application Ser. No. 29/626,652, filed Nov. 17, 2017. These applications are incorporated by reference herein, for all purposes.

BACKGROUND OF THE INVENTION

The present invention relates to the field of sanitation of liquids in a hand-held portable bottle. The inventors of the present invention have been concerned with the proliferation of disposable bottles, e.g. single serve water bottles, in the environment. The Chinese people are becoming healthier and turning away from sodas, the consumption of water has greatly increased. This increase in consumption, unfortunately has been associated with an increase in the number of disposable water bottles that are being used and thrown away. Although plastic recycling captures a portion of the disposed bottles, a large amount of these bottles work their way to forests, watersheds, and other environmentally sensitive areas.

A solution to reduce the amount of waste has been the use of refillable water bottles made of plastics, stainless steel, glass, or the like. In typical use, the inventors have discovered that many users do not clean their water bottles between uses and use them for weeks without cleaning. One reason for this is that it is almost impossible to scrub the interior of such bottles without the use of special brushes. Another reason for this lack of hygiene has typically been that users believe that since the bottle only stores water, the bottle will not be contaminated. The inventors have run multiple experiments to prove that this belief is incorrect, and the inventors have proven that the interior of such bottles can incubate bacteria from the users' mouths or from the water quite effectively. After a week of use, the amount of bacteria or other pathogens in the water and water bottles can be quite unhealthy. In light of the above, what is desired are methods and devices for storing liquids without the drawbacks discussed above.

SUMMARY

The present invention relates to the field of sanitation of liquids in a hand-held portable bottle. According to one aspect of the invention, a portable hand-held device configured to store liquids is disclosed including a liquid storage portion comprising an exterior surface and an interior surface, wherein a user is configured to contact the exterior surface during user consumption, wherein the interior surface forms a water-tight region configured to store liquids, and a material configured to reflect ultraviolet light. A device may include a cap coupled to the liquid storage portion for releasably sealing the water-tight region. A cap may include: a power source for providing operating power, a UV light source coupled to the power source and for selectively proving UV light, wherein the UV light source is disposed within the cap such that the UV light is directed to the water-tight region when the cap seals the water-tight region, a light sensor coupled to the power source within the cap such that ambient light, if any, within the vicinity of the UV light source upon the cap can be sensed, wherein the light sensor is for determining a light condition when the ambient light is sensed and for providing a dark condition when the ambient light is not sensed, a button coupled to the power source, wherein the button is for receiving a user selection, a processor coupled to the power source, the UV light source, to the light sensor and to the button, wherein the processor is for selectively directing the UV light source to provide the UV light in response to the dark condition and the user selection.

According to another aspect of the invention, a method for a portable hand-held device configured to store liquids is described. A technique includes disposing water in an interior storage region of a housing, comprising a material for reflecting ultraviolet light, coupling a cap to the housing such that the interior storage region and the cap form a water-tight region, receiving a push of a button disposed upon the cap by a user, determining with a light sensor whether visible light, if any, is present in a vicinity of a UV light source disposed within the cap, in response to the push of the button. A process includes initiating providing with a UV light source UV light to the water-tight region in response to the push of the button and in response to determining absence of the visible light being present in the vicinity of the UV light source, and inhibiting providing with the UV light source the UV light to the water-tight region after a period of time after the initiating providing UV light to the water-tight region or in response to determining the visible light being present in the vicinity of the UV light source.

According to another aspect of the invention, a portable hand-held device configured to store liquids is disclosed. One device includes a liquid storage portion comprising an exterior surface and an interior surface, wherein a user is configured to contact the exterior surface during consumption of the liquids, wherein the interior surface forms a water-tight region configured to store liquids, and a cap coupled to the liquid storage portion, wherein the cap is configured to releasably seal the water-tight region. In some embodiments, the device includes an identifier configured to allow a separate external apparatus to identify the device, wherein the unique indicator is selected from a group consisting of: optical identifier (a 1D or 2D bar code, QR code, holographic tag), an NFC tag, and short range rf identifier and a wireless identification tag.

According to another aspect of the invention, a device configured to store liquids is described. An apparatus may include a liquid storage portion comprising a top portion and a bottom portion, wherein the liquid storage portion comprises a UV blocking material. A device may include an insert disposed between the top portion and the bottom portion, wherein the insert includes: a power source configured to provide operating power, a UV LED light source coupled to the power source and configured to selectively provide UV light, wherein the UV LED light source is configured to provide UV light toward the bottom portion, and a processor coupled to the power source, the UV LED light source, wherein the processor is configured to periodically direct the UV LED light source to the bottom portion to thereby sanitize the liquids stored in the bottom portion. An insert may include a filter region configured to receive a filter bag, and a filter bag disposed in the filter region, wherein the filter bag is configured to filter particulate contamination of the liquids passing therethrough. In various embodiments, the liquids pass from the top portion through the insert to the bottom portion in response to gravity.

According to another aspect of the invention a liquid dispensing station and a method are disclosed. A process may include receiving with a processor, a bottle identifier in response to an identifier disposed upon or stored in a portable hand-held water storage device, wherein the identifier is selected from a group consisting of: an optical bar code, an rf tag, and a digital code, determining with the processor, a liquid service level associated with the bottle identifier. A technique may include dispensing a liquid in response to the liquid service level, wherein characteristics of the liquid may be modified in response to the liquid service level, wherein the characteristics are selected from a group consisting: liquid supplier, liquid brand, temperature, and carbonation.

BRIEF DESCRIPTION OF THE DRAWINGS

In order to more fully understand the present invention, reference is made to the drawings. These drawings are not to be considered limitations in the scope of the invention, the presently described embodiments and the presently understood best mode of the invention are described with additional detail through use of the accompanying drawings in which.

DETAILED DESCRIPTION

Figure 1:
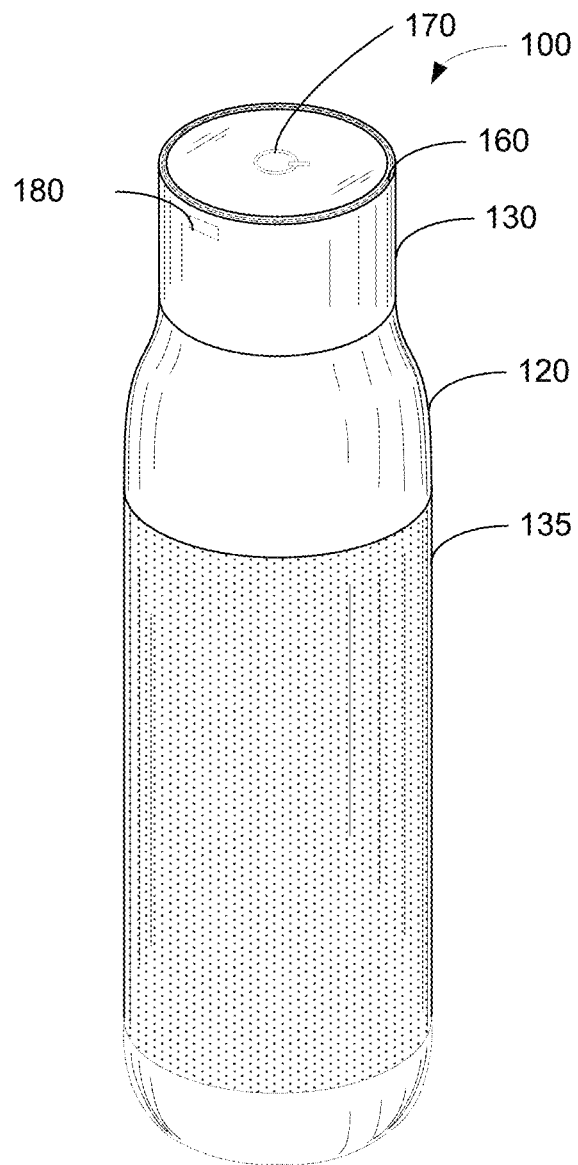
FIGS. 1-3 illustrate external views of embodiments of the present invention.
Figure 2:
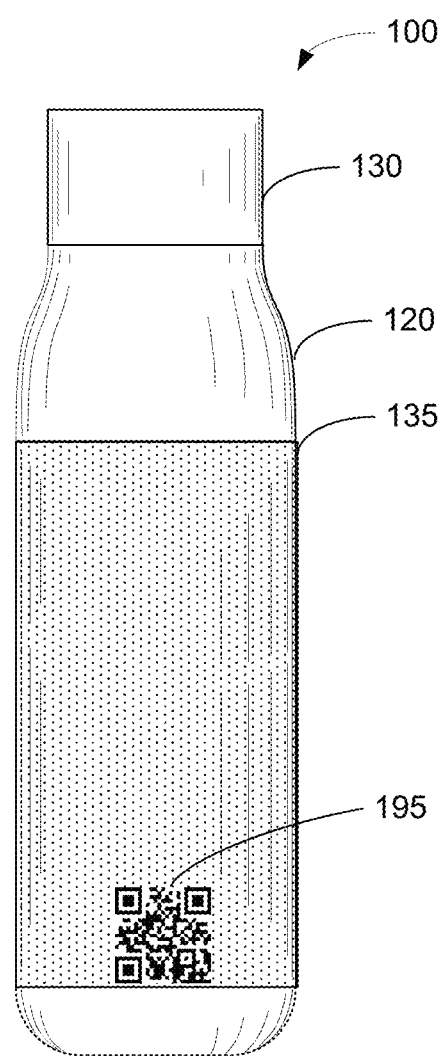
Figure 3:
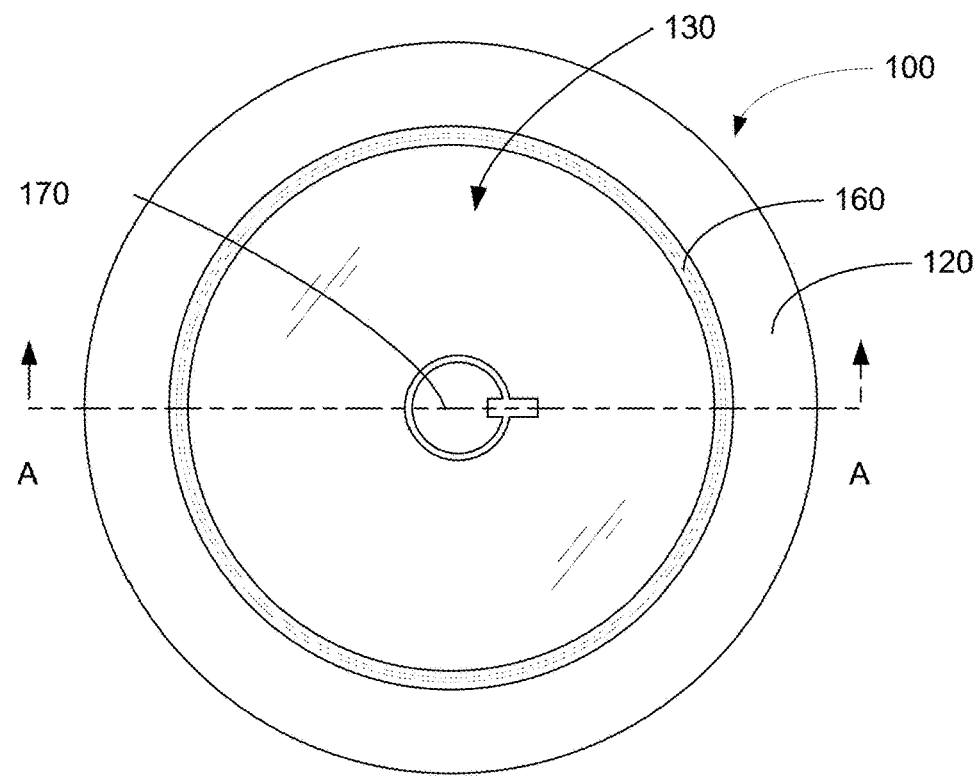

FIGS. 1-3 illustrate external views of an embodiment of a water bottle 100 according to embodiments of the present invention. In FIGS. 1-3, water bottle typically includes an insulated bottom portion 120 and a cap portion 130. Insulated bottom portion 120 typically includes an external housing wall 135 (for the user to hold); an interior wall (for storage of the liquid); and an insulating region (e.g. vacuum, fiberglass, Styrofoam, etc.) between the walls. Typical materials for external housing wall 135 and interior wall includes UV reflective materials, such as stainless steel, aluminum, or the like. In various embodiments external housing wall 135 may be painted, coated, anodized, or the like.

In some embodiment, cap portion 130 includes a ring-like illumination region 160, a user pushable button 170, and a port 180. Region 160 along with one or more LEDs 165 can be used to visually indicate to a user the status of a UV illumination process by combinations of color, color patterns, and intensity. In some examples, illumination patterns may include a chase, heartbeat, blinking or steady; color may indicate status, e.g. blue for UV illumination, completion with green color, interruption of the process with red color, low power with yellow, and the like. In various embodiments, port 180 may be a micro USB port, USB-C port or any other type of port for charging of a power source 220 within cap portion 130, and/or for communicating with processor 230 and memory 240 components disposed within cap portion 130. In various embodiments, button 170 is disposed beneath a flexible material 175, e.g. rubber, silicone, or the like, and the material 175 is deformed when the user pushes button 170 and returns to its original state thereafter. In other embodiments, a wireless charging interface may be provided, such as a Qi charging interface, and others.

Figure 4:
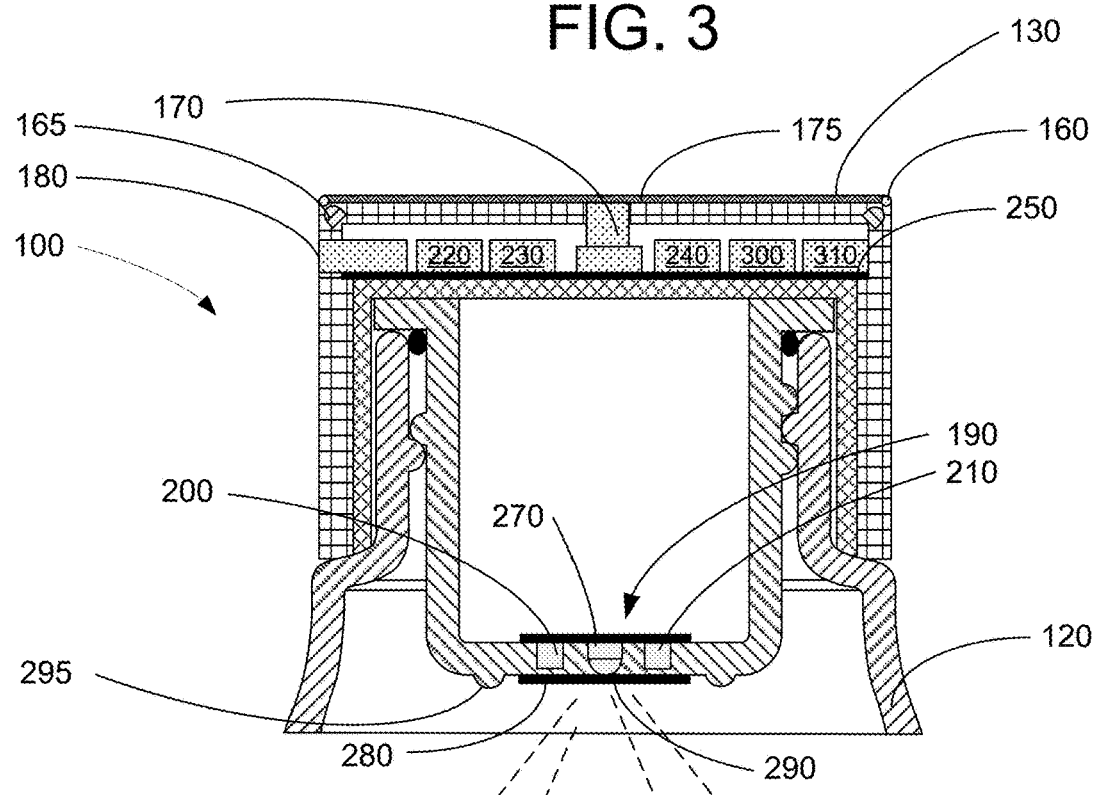
FIG. 4 illustrates a cross-section diagram according to various embodiments.

FIG. 4 illustrates a cross-section 110 of a portion of water bottle 100 according to various embodiments. In various embodiments, cap portion 130 includes a power source 220, processor or controller 230, and a memory 240 mounted upon a printed circuit board (flexible or rigid) 250. Additionally, cap portion 130 includes a UV-LED module 190, a thermistor 200, and a photo sensor 210. In some embodiments, these components may be mounted on a rigid or flexible printed circuit board 270, or the like. The components described herein for cap portion 130 may be coupled by one or more communication and power busses.

In various embodiments, UV-LED module 190 is configured to provide UV illumination within the UV-C band. UV-LEDs provided by the assignee of the present invention may be used in some embodiments. UV-LED module 190 typically includes a UV-LED 290 disposed within or behind a non-toxic UV transparent media 280, e.g. sapphire, fused glass, Zinc selenide (ZnSe), calcium fluoride (CaF2), lithium fluoride (LiF), magnesium fluoride (MgF2), quartz, or the like. As can be seen, UV light projects downwards into the liquid storage region.

In various embodiments, thermistor 200 is disposed near UV-LED module 190 and is used to determine a temperature near the UV-LED module 190 at the bottom surface of cap portion 130. The temperature can be used to determine whether UV-LED module 190 is operating below a preset maximum temperature. Photo sensor 210 is provided for detection of ambient light. In operation, if light strikes photo sensor 210, it can be assumed that cap portion 130 is unscrewed or unsecured relative to bottom portion 120. In such a case, it may be unsafe to active UV-LED module 190 and to output UV light. Accordingly, in some embodiments, when photo sensor 210 does not detect light then UV-LED module 190 may output UV light (under direction of the processor 230). In some embodiments, photo sensor 210 will not sense light when UV-LED module 190 outputs UV light, due to the inclusion of a UV blocking window 280 in front of photo sensor 210. As illustrated in FIG. 4, bumps 295 may be placed upon the bottom of cap portion 130 to protect damage to transparent media 280 when cap portion 130 is placed on a surface, e.g. table. In various embodiments, cap 130 is water tight.

Concepts disclosed by embodiments of the present invention include: Methods: using a photo-electrical method to detect light that ensures no environmental light is present to trigger UV light disinfection in a closed enclosure. Devices: the bottle cap with photo sensor (e.g. photodiode) enclosed in a non-transparent bottle vessel or in a UVC light absorbing plastic.

Figures 5, 6:
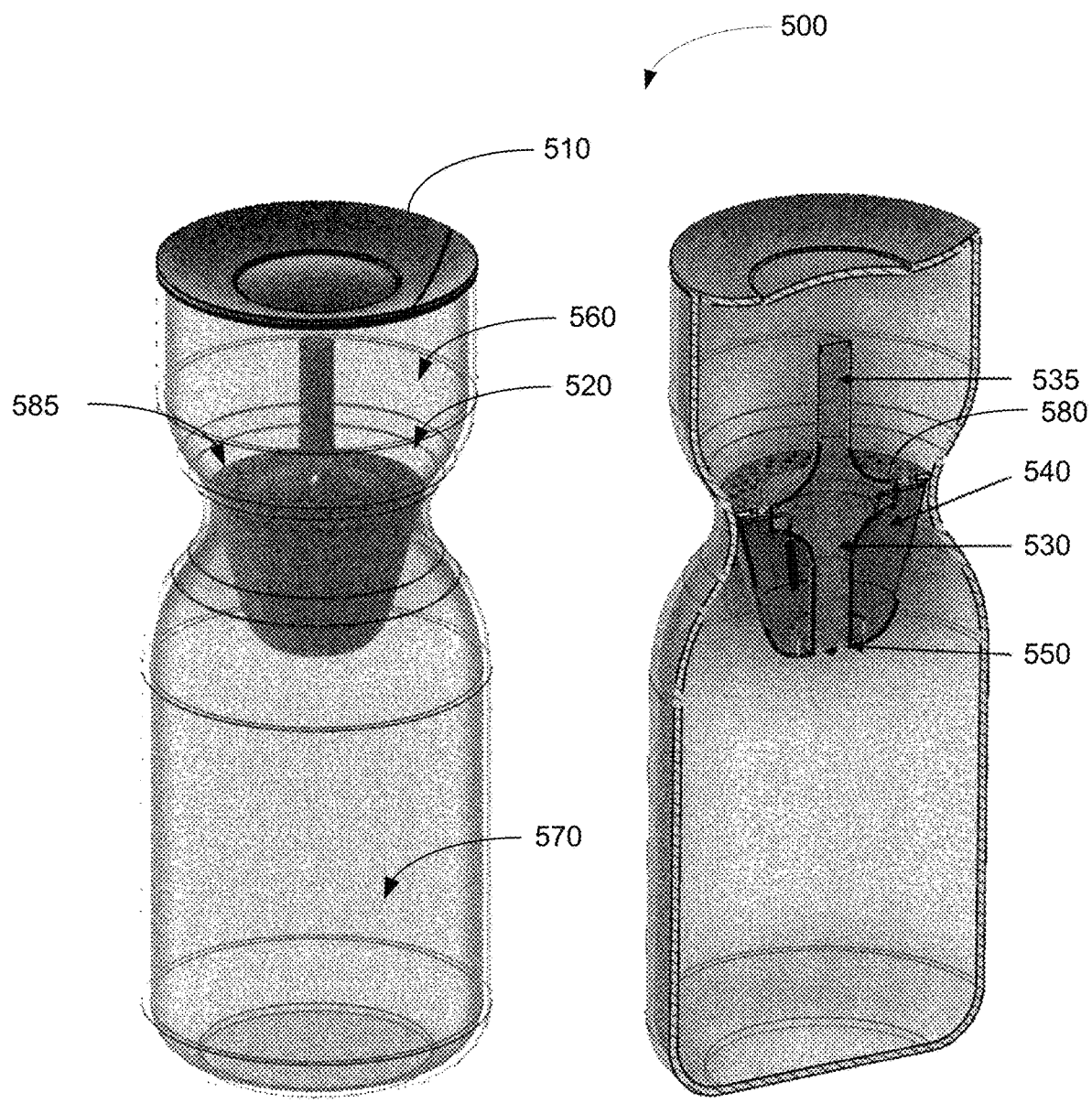
FIG. 5 illustrates an external view of an embodiment of the present invention.
FIG. 6 illustrates a cross-section diagram according to various embodiments.

FIGS. 5 and 6 illustrate various embodiments of the present invention. FIG. 5 illustrates an isometric view of a pitcher 500 and FIG. 6 illustrates a cross-section view of pitcher 500. A pitcher 500 is illustrated including a cap 510 and a module 520. In various embodiments, pitcher 500 may use a transparent or translucent material that is capable of blocking UV light; and cap portion 510 and module 520 may be formed with UV light blocking opaque material. As illustrated, pitcher 500 may have in input reservoir 560 and an output reservoir 570, and module 520 includes a series of holes 580 that allows transport of water, or other liquid from input reservoir 560 to output reservoir 570. In various embodiments, module 520 treats liquids passing therethrough with a chemical/particulate filter and UV light. Module 520 may also treat liquid within output reservoir 570 with UV light. In various embodiments, a one-way valve 585 (e.g. flap, ball valve, etc.) may be included on module 520 allowing water or liquid from output reservoir 570 to be poured out by the user.

In various embodiments, module 520 includes central portion 530 includes electrical components similar to those illustrated in FIG. 4, including a power supply, processor, memory, MEMS accelerometer, wireless communication, and the like; perimeter portion 540 includes a region where filtering materials (e.g. active carbon, and the like) may be enclosed; and bottom portion 550 includes one or more UV LEDs, similar to LED module 190, as illustrated in the embodiments in FIG. 4. In various embodiments, it is contemplated that module 520 may be removed from pitcher 500 for charging the power supply in central portion 530, for changing the filtering materials within perimeter portion 540, or even for replacement. Alternatively, module 520 may be disposed (i.e. thrown away), and a fresh module may be placed within pitcher 500.

In one example operation, a user fills input reservoir 560 with water; water is passed through module 520, which filters-out chemical and particulate matters; and the water is passed into output reservoir 570. Periodically, UV LEDs in module 520 are directed to output UV light within module 520, to inhibit growth of bacteria, or other biological materials within the filtering material. Additionally, periodically (e.g. 1 minute every 1, 2, etc. hours) UV light may be directed to water stored within output reservoir 570 also to inhibit biological contamination of the water. In some embodiments, as a safety measure, one or more positional sensors may be used within module 520 relative to pitcher 500. In some embodiments, UV light will not be output from UV LEDs unless the positional sensors indicate proper positioning of module 520 within pitcher 500. In some embodiments, the positional sensors may include a tab extending from the wall of pitcher 500 which is sensed by an optical sensor within module 520, or the like.

According to various embodiments, concepts disclosed by embodiments of the present invention include methods and apparatus: Using a UV light source as part of a filter cartridge where the water is being filter and UV disinfected; Using a UV light source w/battery and recharge electronics as part of a filter cartridge; Using a UV light source as part of a filter cartridge where the UV light keeps the filtered water clean and bacteria free; Using a UV light source as part of a filter cartridge where UV light is used in combo with a sensor to measure the water flow volume thru a filter as a "tracker" and counter for changing the filter medium. Other embodiments may include: using a Wi-Fi/Bluetooth for tracking hydration and or paring with other devices; using a replaceable filter media pouch bags that excludes a hard-plastic shell; Using a water pitch that does not have a hopper as traditional pitcher does (Brita like). The filter has two modes: one mode to let water go thru via gravity, the other mode to let filtered water pour out (e.g. a ball valve or 45 degree turn to let water flow in/out).

In various embodiments, designs for a water pitcher are contemplated. Design embodiments includes the shape of the plastic or glass (translucent) water pitcher (with or without the cap), wherein the diameter of the top portion 560 is substantially the same as the diameter of bottom portion 570, and the sidewalls may be approximately cylindrical and perpendicular to a bottom. In some embodiments, the tapering of the pitcher may or may not be symmetric as it approaches module 520. Further the curved bottom may or may not be part of the design. The contour lines may or may not be part of the design in various embodiments. Other separate or additional design embodiments to the above embodiments is the shape of module 520, as shown, having a curved and tapered upper portion or a tapered then curved bottom portion, or both. The module 520 may have an overall circular shape with a top surface with circular holes, square holes, or other shape holes 580. Other separate or additional design embodiments to the above embodiments includes a cap having a downward sloping curved portion and a curved convex region.

Embodiments of the present invention may include external communication mechanisms (e.g. 300), such as Wi-Fi, Bluetooth, NFC, 2D Barcodes, QR code, Zig-Bee, and the like, (e.g. 195) as described below. In some embodiments, a liquid dispensing terminal may first communicate with the liquid storage device, e.g. laser scan, rf excitation, or the like. Next, in such embodiments, the liquid storage device may identify itself to the dispensing terminal. For example, a barcode may be read by the liquid dispensing terminal, a responsive rf signal may be provided to the liquid dispensing terminal, and the like to determine a bottle identifier. In some embodiments, the user may scan or swipe a card, or the user may type a password or use biometric data to provide an identifier to the liquid dispensing terminal.

The liquid dispensing terminal may then determine what type of water service is associated with the bottle identifier (e.g. user water-type service subscription, water-service provider, etc.). Subsequently, in response to the identification and/or the service level subscribed, the dispensing terminal may dispense specific liquids. For example, a dispensing terminal may dispense Evian water or Fiji water, depending upon the identification provided by the device. Thus, a user of the storage device may subscribe to Fiji water, thus at an airport, when they refill their bottle, Fiji water is automatically provided. To non-subscribers, regular filtered tap water may be provided.

In other embodiments, the bottle can use Wi-Fi to pair with a hydration refill station (think of the water fountain you see in airports) where it offers "branded" premium water, e.g. Evian, where the owner of the liquid storage device or bottle gets two years of free refill of such branded premium water, after purchase of the liquid storage device (e.g. Evian-branded water bottle). After two years, this may become a monthly subscription model where the user of Evian-branded bottle can refill with Evian for a monthly fee. In some embodiments, branded water bottles may be given away for free, and the hydration refill stations and systems may provide premium water for the first 90 days. After that, premium water can be provided based upon a water subscription (e.g. $10 per month), a pay-per-use model (e.g. $2 to fill-up), or the like. In other embodiments, user preferences may be incorporated with the dispensing of the water. For example, a first user's water-subscription may specify a lemon essence is to be added to water, whereas a second user's water-subscription may specify a specific temperature water (e.g. boiling, room temperature, chilled), and the like.

Embodiments of the present invention now enable premium bottled water brands to reduce plastic pollution by enabling users to obtain premium bottled water. In various embodiments, hydration fill stations may include one or more stainless steel storage containers that store the premium water brands. When nearly empty, such hydration fill stations may wirelessly communicate with the premium water distributor (e.g. of Fiji, etc.) and indicate that a refill is necessary. Such embodiments are beneficial as they reduce the amount of plastic and packaging waste, reduce the amount of delivery locations for the water, and the like. This may also help better forecast shipping water globally since the end terminal consumption points are now connected with data (their tanks). In some embodiments, UV LEDs are provided in the stainless-steel tanks to keep the premium water in such locations for as long as needed until they are consumed.

In other embodiments, combinations or sub-combinations of the above disclosed invention can be advantageously made. For example, in various embodiments, thermistor 200 determines a temperature near the UV-LED module 190 at the bottom surface of cap portion 230. It should be understood that the temperature of the liquid or water can affect the temperature reading of thermistor 200. For example, if ice water is stored, the temperature measured may reflect the temperature of the ice water, as heat produced by UV-LED module 190 is highly dissipated, cooled, by the ice water. Conversely, if boiling water is stored, the temperature measured may reflect the temperature of the boiling water, or higher, as it is more difficult to dissipate the heat produced by UV-LED module 190 into the boiling water. In various embodiments, when the temperature exceeds a threshold temperature, power to UV-LED module 190 may be shut off. Accordingly, it is more likely that power may be shut off from UV-LED module 190 when hot liquids are stored compared to when cooler liquids are stored. The water temperature can thus be inferred by the readings from thermistor 200.

In other embodiments, additional functionality may be provided. For example, embodiments may include additional modules 310 that embody: a positional sensor (already described herein) e.g. a MEMS accelerometer; a wireless communication module (already described herein), e.g. NFC, Wi-Fi, Bluetooth, etc.; an audio output device (e.g. piezo electric, speaker); and the like. In light of the present patent disclosure, one of ordinary skill in the art will recognize additional functionality may be added to the embodiments described herein.

The specification and drawings are, accordingly, to be regarded in an illustrative rather than a restrictive sense. It will, however, be evident that various modifications and changes may be made thereunto without departing from the broader spirit and scope of the invention as set forth in the claims.

What is claimed:

1. A portable hand-held device configured to store liquids comprising:
   a liquid storage portion; and
   a cap removably coupled to the liquid storage portion,
   wherein the cap is configured to releasably seal the liquid storage portion, wherein the cap comprises:
      a UV LED light source configured to selectively provide UV light, wherein the UV LED light source is disposed within the cap such that the UV light is directed at the liquid storage portion in response to the cap being set in a position to seal the liquid storage portion;
      a user input device configured to receive a user selection from a user;
      a light sensor disposed within the cap such that, in response to the user selection of the user input device, ambient light is sensed by the light sensor;
      in response to the ambient light being within a vicinity of the UV LED light source and upon the cap, the light sensor is configured to provide a light condition, and in response to the ambient light not being sensed by the light sensor, the light sensor is configured to provide a dark condition; and
      the UV LED light source provides the UV light in response to the dark condition and in response to the user selection of the user input device.

2. The device of claim 1, wherein the cap further comprises a position sensor configured to determine a safe orientation of the cap and wherein the UV LED light source provides the UV light in response to the safe orientation of the cap.

3. The device of claim 1, wherein the cap comprises a window that absorbs a majority of the UV light; wherein the light sensor is configured to sense visible light; and wherein the light sensor is disposed behind the window in the cap such that the majority of the UV light does not reach the light sensor.

4. The device of claim 1, wherein the cap further comprises: a visual indicator ring disposed upon a top portion of the cap, and wherein the visual indicator ring is configured to provide user-viewable illumination in response to the UV LED light source providing the UV light to the liquid storage portion.

5. The device of claim 4, wherein the visual indicator ring provides output of a first color illumination in response to the UV LED light source providing the UV light to the liquid storage portion, and wherein the visual indicator ring provides output of a second color illumination in response to the UV LED light source finishing providing the UV light to the liquid storage portion.

6. The device of claim 1, wherein the cap further comprises a thermistor, wherein the thermistor is configured to determine a temperature within a vicinity of the cap.

7. The device of claim 1, further comprising an identifier configured to allow a separate external apparatus to identify the user, wherein the identifier is selected from a group consisting of: optical identifier, a bar code, a 1D bar code, a 2D bar code, a QR code and a holographic tag.

8. The device of claim 1, further comprising an identifier configured to allow a separate external apparatus to identify the user, wherein the identifier is selected from a group consisting of: an rf tag, a NFC1 tag, a short range rf identifier and a wireless identification tag.

9. A method comprising:
   receiving a selection of a user input device disposed upon a cap of a liquid storage portion configured to store water;
   determining with a light sensor whether visible light is present in a vicinity of a UV LED light source disposed within the cap, in response to the selection of the user input device;
   providing with a UV LED light source UV light to the liquid storage portion in response to the selection of the user input device and in response to determining absence of the visible light being present in the vicinity of the UV LED light source; and
   inhibiting the UV LED light source from providing the UV light to the liquid storage portion at least one of after a period of time or in response to determining the visible light being present in the vicinity of the UV LED light source.

10. The method of claim 9, further comprising:
    determining an indicator signal in response to a predetermined amount of elapsed time;
    determining a physical position of the cap; and
    periodically initiating UV light by the UV LED light source, in response to determining absence of the visible light being present in the vicinity of the UV LED light source, the indicator signal and the physical position of the cap.

11. The method of claim 9, further comprising providing with a visual indicator ring disposed upon a top portion of the cap, a first user-viewable illumination in response to providing with the UV LED light source the UV light to the liquid storage portion.

12. The method of claim 11, further comprising providing with the visual indicator ring disposed upon the top portion of the cap with a second user-viewable illumination in response to inhibiting the UV light from the UV LED light source from the liquid storage portion and wherein the second user-viewable illumination comprises output of a second color illumination, wherein the first user-viewable illumination comprises output of a first color illumination.

13. The method of claim 9 further comprising:
determining with a thermistor disposed within the cap a temperature of the water disposed in the liquid storage portion; and
performing an action in response to the temperature of the water.

14. The method of claim 9, further comprising:
receiving an inquiry by an external apparatus for an identifier associated with the device;
providing the identifier associated with the device to the external apparatus; and
receiving water from a first water source from a plurality of water sources from the external apparatus, wherein the first water source is associated with the identifier.

15. The method of claim 14, wherein the receiving the inquiry comprises receiving a laser scan from the external apparatus; wherein the providing the identifier comprises reflecting the laser scan from a target to provide a response; and wherein the target is selected from a group consisting of: an optical identifier, a bar code, a 1D bar code, a 2D bar code, a QR code and a holographic tag.

16. The method of claim 14, wherein the receiving the inquiry comprises receiving an rf signal from the external apparatus; wherein the providing the identifier comprises responding to the rf signal from a tag to provide a response; and wherein the tag is selected from a group consisting of: an rf tag, a NFC tag, a short range rf identifier and a wireless identification tag.

17. The method of claim 14, wherein the receiving the inquiry comprises receiving an rf signal from the external apparatus; wherein the providing the identifier comprises responding to the rf signal with a rf communications system to provide a response; and wherein the rf communications system is selected from a group consisting of: Wi-Fi, Bluetooth, Zig-Bee, cellular system, LTE, CDMA, GSM.

18. The device of claim 1, wherein the user input device is a button.

19. The device of claim 1, wherein the liquid storage portion comprises an exterior surface having a material configured to block ultraviolet light.

20. The device of claim 1, wherein the liquid storage portion comprises an interior surface having a material configured to reflect ultraviolet light.

* * * * *